United States Patent [19]

Kung et al.

[11] Patent Number: 4,921,637

[45] Date of Patent: May 1, 1990

[54] NAPHTHOQUINONE DERIVATIVES

[75] Inventors: Teh-Ming Kung, Rochester; William B. Vreeland, Webster; Ralph H. Young, Rochester, all of N.Y.

[73] Assignee: Eastman Kodak Company, Rochester, N.Y.

[21] Appl. No.: 287,946

[22] Filed: Dec. 21, 1988

[51] Int. Cl.$^5$ .......................................... C07C 121/48
[52] U.S. Cl. ..................... 552/295; 430/58; 430/59
[58] Field of Search ..................... 260/396 N

[56] References Cited

U.S. PATENT DOCUMENTS

| | | | |
|---|---|---|---|
| 3,615,414 | 10/1971 | Light | 96/1.6 |
| 4,175,960 | 11/1979 | Berwick et al. | 430/58 |
| 4,474,865 | 10/1984 | Ong et al. | 430/58 |
| 4,514,481 | 4/1985 | Scozzafava et al. | 430/58 |
| 4,559,287 | 12/1985 | McAneney et al. | 430/59 |
| 4,578,220 | 3/1986 | Huenig et al. | 260/396 N X |
| 4,578,334 | 3/1986 | Borsenberger et al. | 430/59 |
| 4,606,861 | 8/1986 | Ong et al. | 260/351 |
| 4,609,602 | 9/1986 | Ong et al. | 430/58 |
| 4,666,802 | 5/1987 | Hung et al. | 430/58 |
| 4,701,396 | 10/1987 | Hung et al. | 430/58 |
| 4,719,163 | 1/1988 | Staudenmayer et al. | 430/58 |

FOREIGN PATENT DOCUMENTS 62-32465  2/1987  Japan .

*Primary Examiner*—Vivian Garner
*Attorney, Agent, or Firm*—David F. Janci

[57] ABSTRACT

New chemical compounds are derivatives of certain substituted 1,4-naphthoquinones in which the keto oxygens at the 4-positions have been replaced by certain cyanoalkoxycarbonylmethylene groups, and the keto oxygens at the 1-positions have been replaced by cyanoimino groups. The new compounds have the structure

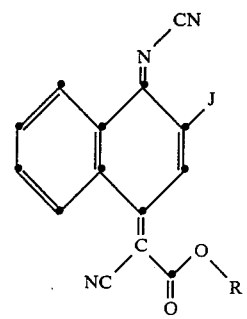

wherein: J is alkyl having 1 to 6 carbon atoms, and R is normal alkyl having 1 to 6 carbon atoms. The compounds are useful as electron-transport agents in electrophotographic elements.

2 Claims, No Drawings

4,921,637

NAPHTHOQUINONE DERIVATIVES

FIELD OF THE INVENTION

This invention relates to new chemical compounds, which are derivatives of 1,4-naphthoquinone. The new compounds can be relatively simply prepared; they have good solubility or dispersibility in organic solvents and polymeric binders; and they can be incorporated in electrophotographic elements, wherein they exhibit unexpectedly good electron-transport properties.

BACKGROUND

In electrophotography an image comprising a pattern of electrostatic potential (also referred to as an electrostatic latent image), is formed on a surface of an electrophotographic element comprising at least an insulative photoconductive layer and an electrically conductive substrate. The electrostatic latent image is usually formed by imagewise radiation-induced discharge of a uniform potential previously formed on the surface. Typically, the electrostatic latent image is then developed into a toner image by contacting the latent image with an electrographic developer. If desired, the latent image can be transferred to another surface before development.

In latent image formation the imagewise discharge is brought about by the radiation-induced creation of electron/hole pairs, which are generated by a material (often referred to as a charge-generation or photoconductive material) in the electrophotographic element in response to exposure to the imagewise actinic radiation. Depending upon the polarity of the initially uniform electrostatic potential and the type of materials included in the electrophotographic element, either the holes or the electrons that have been generated migrate toward the charged surface of the element in the exposed areas and thereby cause the imagewise discharge of the initial potential. What remains is a non-uniform potential constituting the electrostatic latent image.

Most electrophotographic elements currently in use are designed to be initially charged with a negative polarity. Such elements contain material which facilitates the migration of positive holes toward the negatively charged surface in imagewise exposed areas in order to cause imagewise discharge. Such material is often referred to as a hole-transport agent. In elements of that type a positively charged toner material is then used to develop the remaining imagewise unexposed portions of the negative polarity potential (i.e., the latent image) into a toner image. Because of the wide use of negatively charging elements, considerable numbers and types of positively charging toners have been fashioned and are available for use in electrographic developers. Conversely, relatively few high quality negatively charging toners are available.

However, for some applications of electrophotography it is more desirable to be able to develop the surface areas of the element that have been imagewise exposed to actinic radiation, rather than those that remain imagewise unexposed. For example, in laser printing of alphanumeric characters it is more desirable to be able to expose the relatively small percentage of surface area that will actually be developed to form visible alphanumeric toner images, rather than waste energy exposing the relatively large percentage of surface area that will constitute undeveloped background portions of the final image. In order to accomplish this while still employing widely available high quality positively charging toners, it is necessary to use an electrophotographic element that is designed to be positively charged. Thus, positive toner can then be used to develop the exposed surface areas (which will have relatively negative electrostatic potential after exposure and discharge, compared to the unexposed areas, where the initial positive potential will remain).

An electrophotographic element designed to be initially positively charged should, however, contain an adequate electron-transport agent (i.e., a material which adequately facilitates the migration of photogenerated electrons toward the positively charged insulative element surface). Unfortunately (and analogous to the situation with positive and negative toners), many materials having good hole-transport properties have been fashioned for use in electrophotographic elements, but relatively few materials are known to provide good electron-transport properties in electrophotographic elements.

A number of chemical compounds having electron-transport properties are described, for example, in U.S. Pat. Nos. 4,175,960; 4,514,481; 4,474,865; 4,559,287; 4,606,861; and 4,609,602 and in Japanese published Patent Application 62-32465. However, many prior art compounds have one or more drawbacks.

Some prior art electron-transport agents do not perform the electron-transporting function very well, especially under certain conditions or when included in certain types of electrophotographic elements.

Also, some electron-transport agents cause an undesirably high rate of discharge of the electrophotographic element before it is exposed to actinic radiation (often referred to as high dark decay).

Some prior art electron-transport compounds are not soluble or dispersible or have relatively limited solubility or dispersibility in coating solvents of choice or in certain polymeric binders desired to be used in charge-transport layers, such that attempts to include sufficient amounts of such electron-transport agents in electrophotographic elements result in some crystallization of the electron-transport agents, which in turn causes problems such as undesirable levels of dark decay and such as unwanted scatter or absorption of actinic radiation intended to pass undisturbed through the charge-transport layer to a radiation-sensitive portion of the element.

Also, some electron-transport agents suffer from being obtainable only through difficult and/or lengthy methods of preparation.

Thus, there is a need for chemical compounds that will exhibit good electron-transport properties in electrophotographic elements without imparting unacceptably high dark decay properties thereto, that are sufficiently soluble or dispersible in coating solvents and polymeric binders of choice, and that can be readily prepared by relatively simple methods.

SUMMARY OF THE INVENTION

The present invention meets the above-noted need by providing new chemical compounds, which are derivatives of naphthoquinone, having the structure

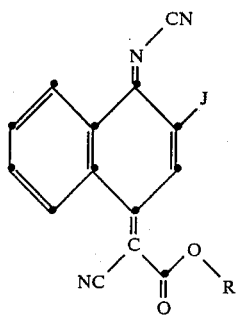

(I)

wherein: J is alkyl having 1 to 6 carbon atoms, and R is normal alkyl having 1 to 6 carbon atoms.

The naphthoquinone derivatives of the invention can be readily prepared by relatively simple methods. They have good solubility or dispersibility in many coating solvents and in many film-forming polymeric binders that are useful to form one or more layers in electrophotographic elements. In electrophotographic elements, the new compounds can serve as electron-transport agents with good capability of accepting and transporting electrons generated by radiation-activated charge-generation materials in the elements, and they do not impart unacceptably high dark decay properties to the elements.

It should be noted that other new chemical compounds, different from those of the present invention, but devised to serve similar purposes, are described in copending U.S. patent application 287,948, filed Dec. 21, 1988. Also, inventive electrophotographic elements containing electron-transport agents comprising the compounds of this invention or other compounds, are described in copending U.S. patent applications 287,947; 287,949; and 287,950, all filed Dec. 21, 1988.

DESCRIPTION OF PREFERRED EMBODIMENTS

The naphthoquinone derivatives of the invention can be conveniently prepared from readily available starting materials, for example, by combining a naphthoquinone having the previously described appropriate J substituent with 1.2 equivalents of the appropriate $C_1$–$C_6$-n-alkyl cyanoacetate in an inert organic solvent in the presence of 2-3 equivalents of titanium tetrachloride. This is followed by a reaction with 2 equivalents of bis-(trimethylsilyl)-carbodiimide in an inert organic solvent in the presence of 2-3 equivalents of titanium tetrachloride. Examples of suitable solvents for both reactions are dichloromethane, acetonitrile, trichloroethane, and dichloroethane.

When the appropriately J-substituted naphthoquinone is not readily commercially available, it can be easily prepared by known methods from readily available materials. For example, 2-ethyl-1,4-naphthoquinone can be prepared from 2-ethylnaphthalene on oxidation with $CrO_3$ in ca. 80% acetic acid at 45°–50° C., and 2-ethylnaphthalene can be prepared by combining naphthalene, ethyl chloride, and $AlCl_3$ in an appropriate solvent, such as carbon disulfide or cyclohexane.

Also, when the appropriate $C_1$–$C_6$-n-alkyl cyanoacetate is not readily commercially available, it can be easily prepared by known methods from readily available materials. For example, n-hexyl cyanoacetate can be prepared from cyanoacetic acid reacted with oxalyl chloride to form cyanoacetyl chloride, followed by reaction with n-hexanol.

A specific example of a preferred embodiment of the inventive Structure (I) compounds, that has been simply prepared and has the advantageous properties previously noted, when employed as an electron-transport agent in electrophotographic elements, is one wherein J is methyl, and R is ethyl.

Some specific examples of compounds outside the scope of Structure (I) that are not part of the present invention, because attempts to prepare them failed, are those wherein (referring to Structure (I) for convenience):

J is methyl, and R is t-butyl;

R is ethyl, and J is H, propylthio, tolylthio, tolylsulfinyl, propylsulfonyl, or tolylsulfonyl; and also compounds having the structures:

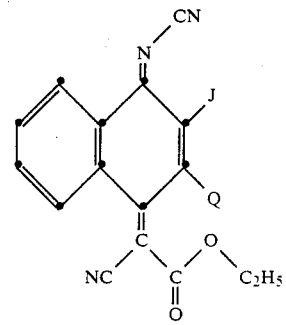

wherein:

J is H, and Q is —S—$C_6H_5$ or —SO—$C_6H_5$; or

J is methyl, and Q is —S—$C_3H_7$ or —SO—$C_3H_7$; and

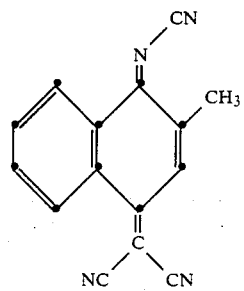

Some specific examples of compounds outside the scope of Structure (I) that are not part of the present invention, because they could not be incorporated in electrophotographic elements in sufficient amounts in a non-crystalline state, because they were too insoluble in commonly used coating solvents (e.g., in tetrahydrofuran, dichloromethane, acetone, acetonitrile, toluene, and/or lower alcohols) and/or were too insoluble in or incompatible with polymeric binders commonly employed in charge-transport layers of electrophotographic elements (e.g., polycarbonates, polyesters, polystyrenes, and/or copolymers of styrenes and acrylates) are those having the structures:

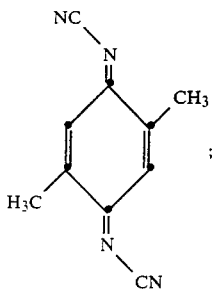

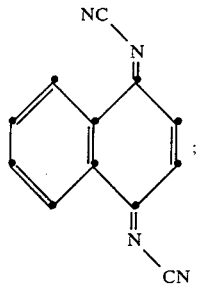

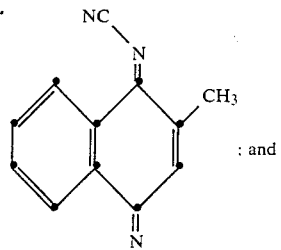

; and

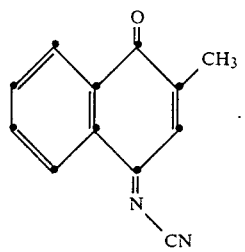

Some specific examples of compounds outside the scope of Structure (I) that are not part of the present invention, because they were unstable over time and caused high dark decay when it was attempted to utilize them as electron-transport agents in electrophotographic elements, are those having the structures:

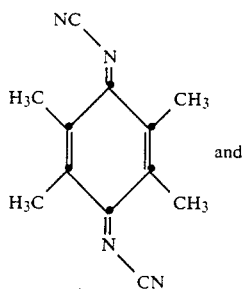

and

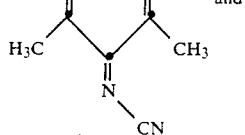

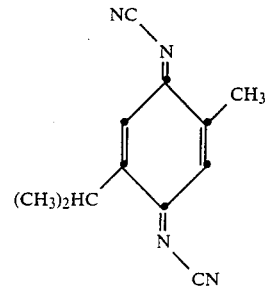

The new chemical compounds of the invention are useful in electrophotographic elements of various types, all of which contain one or more of the new naphthoquinone derivatives of the invention to serve as electron-transport agents in the elements. The various types of elements include both those commonly referred to as single layer or single-active-layer elements and those commonly referred to as multiactive, multilayer, or multi-active-layer elements.

Single layer elements are so named, because they contain only one layer that is active both to generate and to transport charges in response to exposure to actinic radiation. Such elements typically comprise at least an electrically conductive layer in electrical contact with a photoconductive layer. In single layer elements utilizing compounds of the invention, the photoconductive layer contains a charge-generation material to generate electron/hole pairs in response to actinic radiation and an electron-transport material, comprising one of the new naphthoquinone derivatives of the invention, which is capable of accepting electrons generated by the charge-generation material and transporting them through the layer to effect discharge of the initially uniform electrostatic potential. The photoconductive layer is electrically insulative, except when exposed to actinic radiation, and sometimes contains an electrically insulative polymeric film-forming binder, which may itself be the charge-generating material or may be an additional material which is not photoconductive. In either case the electron-transport agent is dissolved or dispersed as uniformly as possible in the binder film.

Multiactive elements are so named, because they contain at least two active layers, at least one of which is capable of generating charge in response to exposure to actinic radiation and is referred to as a charge-generation layer (hereinafter also referred to as a CGL), and at least one of which is capable of accepting and transporting charges generated by the charge-generation layer and is referred to as a charge-transport layer (hereinafter also referred to as a CTL). Such elements typically comprise at least an electrically conductive layer, a CGL, and a CTL. Either the CGL or the CTL is an electrical contact with both the electrically conductive layer and the remaining CGL or CTL. Of course, the CGL contains at least a charge-generation material (a photoconductor); the CTL contains at least a charge-transport agent; and either or both layers can contain an additional film-forming polymeric binder. In multiactive elements utilizing compounds of the invention the charge-transport agent is an electron-transport agent comprising one of the inventive naphthoquinone derivatives.

Single layer and multilayer electrophotographic elements and their preparation and use, in general, are well known and are described in more detail, for example, in U.S. Pat. Nos. 4,701,396; 4,666,802; 4,578,334; 4,719,163; 4,175,960; 4,514,481; and 3,615,414, the disclosures of which are hereby incorporated herein by reference. The only essential difference of electrophotographic elements utilizing compounds of the present invention from generally known elements is that the new elements contain the inventive naphthoquinone derivatives as electron-transport agents.

In preparing single-active-layer electrophotographic elements containing compounds of the invention, the components of the photoconductive layer, including any desired addenda, can be dissolved or dispersed together in a liquid and can be coated on an electrically conductive layer or support. The liquid is then allowed or caused to evaporate from the mixture to form the permanent layer containing from about 10 to about 70 percent (by weight) of the inventive electron-transport agent and from about 0.01 to about 50 weight percent of the charge-generating material. Included among many useful liquids for this purpose are, for example, aromatic hydrocarbons such as benzene, toluene, xylene and mesitylene; ketones such as acetone and butanone; halogenated hydrocarbons such as methylene chloride, chloroform and ethylene chloride; ethers, including ethyl ether and cyclic ethers such as tetrahydrofuran; and mixtures thereof.

In preparing multiactive electrophotographic elements containing compounds of the invention, the components of the CTL can similarly be dissolved or dispersed in such a liquid coating vehicle and can be coated on either an electrically conductive layer or support or on a CGL previously similarly coated or otherwise formed on the conductive layer or support. In the former case a CGL is thereafter coated or otherwise formed (e.g., by vacuum-deposition) on the CTL. The CTL will usually contain from about 10 to about 70 weight percent of the inventive electron-transport agent, although concentrations outside that range may be found to be useful in some cases.

Various electrically conductive layers or supports can be employed in electrophotographic elements containing compounds of the invention, such as, for example, paper (at a relative humidity above 20 percent); aluminum-paper laminates; metal foils such as aluminum foil, zinc foil, etc.; metal plates such as aluminum, copper, zinc brass and galvanized plates; vapor deposited metal layers such as silver, chromium, vanadium, gold, nickel, aluminum and the like; and semiconductive layers such as cuprous iodide and indium tin oxide. The metal or semiconductive layers can be coated on paper or conventional photographic film bases such as poly(ethylene terephthalate), cellulose acetate, polystyrene, etc. Such conducting materials as chromium, nickel, etc. can be vacuum-deposited on transparent film supports in sufficiently thin layers to allow electrophotographic elements prepared therewith to be exposed from either side.

Any charge-generation material can be utilized in elements that contain an electron-transport agent comprising a compound of the invention. Such materials include inorganic and organic (including monomeric, metallo-organic and polymeric organic), photoconductors, for example, zinc oxide, lead oxide, selenium, phthalocyanine, perylene, arylamine, polyarylalkane, and polycarbazole materials, among many others.

When solvent-coating a photoconductive layer of a single-active-layer element or a CGL and/or CTL of a multiactive element, a film-forming polymeric binder can be employed. The binder may, if it is electrically insulating, help to provide the element with electrically insulating characteristics. It also is useful in coating the layer, in adhering the layer to an adjacent layer, and when it is a top layer, in providing a smooth, easy to clean, wear-resistant surface.

The optimum ratio of charge-generation or charge-transport material to binder may vary widely depending on the particular materials employed. In general, useful results are obtained when the amount of active charge-generation and/or charge-transport material contained within the layer is within the range of from about 0.01 to about 90 weight percent, based on the dry weight of the layer.

Representative materials which can be employed as binders in charge-generation and charge-transport layers are film-forming polymers having a fairly high dielectric strength and good electrically insulating properties. Such binders include, for example, styrene-butadiene copolymers; vinyl toluene-styrene copolymers; styrene-alkyd resins; silicone-alkyd resins; soya-alkyd resins; vinylidene chloride-vinyl chloride copolymers; poly(vinylidene chloride); vinylidene chloride-acrylonitrile copolymers; vinyl acetate-vinyl chloride copolymers; poly(vinyl acetals), such as poly(vinyl butyral); nitrated polystyrene; poly(methylstyrene); isobutylene polymers; polyesters, such as poly[ethylene-co-alkylenebis(alkyleneoxyaryl)phenylene-dicarboxylate]; phenolformaldehyde resins; ketone resins; polyamides; polycarbonates; polythiocarbonates; poly[ethylene-co-isopropylidene-2,2-bis(ethyleneoxyphenylene)terephthalate]; copolymers of vinyl haloacrylates and vinyl acetate such as poly(vinyl-m-bromobenzoate-co-vinyl acetate); chlorinated poly(olefins), such as chlorinated poly(ethylene); and polyimides, such as poly[1,1,3-trimethyl-3-(4'-phenyl)-5-indane pyromellitimide].

Binder polymers should provide little or no interference with the generation or transport of charges in the layer. Examples of binder polymers which are especially useful include bisphenol A polycarbonates and polyesters such as poly[4,4'-(2-norbornylidene)diphenylene terephthalate-co-azelate].

CGL's and CTL's can also contain other addenda such as leveling agents, surfactants, plasticizers, sensitizers, contrast-control agents, and release agents, as is well known in the art.

Also, elements containing a compound of the invention can contain any of the optional additional layers known to be useful in electrophotographic elements in general, such as, e.g., subbing layers, overcoat layers, barrier layers, and screening layers.

The following Example is presented to further illustrate the preparation of a preferred compound of the invention and its utility as an electron-transport agent in a multiactive electrophotographic element.

In the Example performance of the element is illustrated in regard to electrophotographic speed (also referred to as sensitivity) and dark decay properties.

In illustrating electrophotographic speed in the Example, the element is electrostatically corona-charged to an initial positive potential and then exposed to actinic radiation (radiation having peak intensity at a wavelength to which the charge-generation material in the element is sensitive in order to generate electron/- hole pairs) in an amount sufficient to photoconductively discharge a certain percentage of the initial voltage (50% or 80% of the initial voltage). Electrophotographic speed is measured in terms of the amount of incident actinic radiant energy (expressed in ergs/cm$^2$) needed to achieve the desired percentage of discharge of the initial voltage. The lower the amount of radiation needed to achieve the desired degree of discharge, the higher is the electrophotographic speed of the element, and vice versa.

In illustrating dark decay properties in the Example, the rate of dissipation of the initial voltage (expressed in V/s, i.e., volts per second) is measured while the element remains in darkness (i.e., before any exposure to actinic radiation). This is accomplished by measuring the initial voltage and the voltage remaining on the element after 2 seconds in darkness and dividing the difference by 2. The lower the rate of discharge in darkness, the better is the dark decay property of the element, i.e., the better is the element's ability to retain its initial potential before exposure.

EXAMPLE

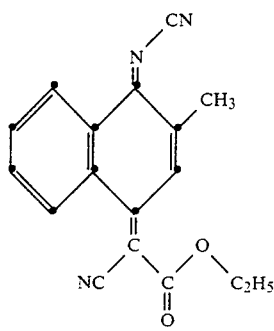
(I-A)

The compound of Structure (I-A) was prepared as follows.

A solution of 80 ml (0.726 moles) TiCl$_4$ in 150 ml CCl$_4$ was added dropwise to 1200 ml dry tetrahydrofuran (THF) at 0° C. under argon. The resulting yellow suspension was quickly added to a 0° C. solution of 50.0 grams (0.29 moles) 2-methylnaphthoquinone obtained from Eastman Kodak Co., USA. 39.42 grams (0.35 mole) ethyl cyanoacetate and 700 ml dry THF. The mixture was stirred for thirty minutes at 0° C. 91.88 grams (1.16 mole) of pyridine was added dropwise over a ten-minute period. The reaction mixture was stirred at room temperature (25° C.) overnight. Two liters of distilled water were added and the organic phase was separated, washed with dilute NaHCO$_3$, then with brine and dried over MgSO$_4$. The resulting yellow solid was recrystallized from ethanol to yield 39 grams of 2-methyl-4-(cyanoethoxycarbonylmethylene)naphthoquinone, of which 5.0 grams (0.019 mole) were then dissolved in 50 ml dichloromethane. The solution was cooled to 0° C. in an ice bath. 4.12 ml of TiCl$_4$ were added to the solution dropwise over a ten minute period. 7.08 grams (0.038 mole) of bistrimethylsilylcarbodiimide, obtained from Petrarch Chemical Co., USA, [structure: (CH$_3$)$_3$Si—N=C=N—Si(CH$_3$)$_3$] were added to the reaction mixture dropwise over a five minute period. The reaction mixture was stirred under argon for 24 hours. 25 ml of water were added to the reaction mixture, and the crude product was collected by filtration. The product was purified by column chromatography to yield 276 mg of the Structure (I-A) compound. Its structure was confirmed by infrared spectroscopy, nuclear magnetic resonance spectroscopy, and combustion analysis.

Glass transition temperature=90°–94° C.

Elemental analysis: calculated for C$_{17}$H$_{13}$N$_3$O$_2$: 14.4% N, 70.1% C, 4.5% H; found: 13.5% N, 70.3% C, 5.0% H.

An electrophotographic element was prepared as follows.

A conductive support was prepared by vacuum-depositing a thin conductive layer of aluminum onto a 178 micrometer thickness of poly(ethylene terephthalate) film.

A charge-generation layer (CGL) was prepared by dispersing the charge-generation material, titanyl tetrafluorophthalocyanine (described more extensively in U.S. Pat. No. 4,701,396), in a solution of a binder comprising a polyester formed from 4,4'-(2-norbornylidene)diphenol and terephthalic acid:azelaic acid (40:60 molar ratio) in dichloromethane (the weight ratio of charge-generation material:binder being 2:1), ball milling the dispersion for 60 hours, diluting with more dichloromethane to achieve suitable coating viscosity, coating the dispersion onto the aluminum-coated side of the conductive support, and drying off the solvent to yield a CGL of 0.5 micrometer thickness.

A coating solution for forming a charge-transport layer (CTL) was then prepared comprising 10 weight percent solids dissolved in dichloromethane. The solids comprised the inventive electron-transport agent of Structure (I-A) above and the same polymeric binder material as employed in the CGL. The weight ratio of electron-transport agent:polymeric binder was 30:70. The solution was then coated onto the CGL and dried to form the CTL on the CGL. The combined thickness of CGL and CTL was 10 micrometers.

The resultant electrophotographic element was corona-charged to an initial uniform positive potential of 422 V.

Dark decay rate of the initial potential was determined to be 26 V/s.

The uniformly charged element was subjected to simulated imaging exposure by exposing it through the outer surface of the CTL to radiation having a peak intensity at a wavelength of 830 nanometers (nm) (to which the charge-generation material is sensitive, in order to generate electron/hole pairs in the CGL) at a rate of 2 ergs of radiant energy per square centimeter of element surface per second (2 ergs/cm$^2$s). The amount of incident actinic radiant energy necessary to discharge a given percentage of the initial uniform potential on the element (i.e., the electrophotographic speed) was determined to be 7.7 ergs/cm$^2$ to discharge 50% of the initial potential and 30 ergs/cm$^2$ to discharge 80% of the initial potential.

The invention has been described in detail with particular reference to certain preferred embodiments thereof, but it should be appreciated that variations and modifications can be effected within the spirit and scope of the invention.

What is claimed is:

1. A chemical compound having the structure

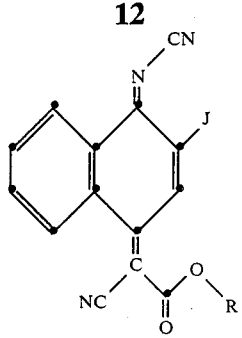
wherein:
J is alkyl having 1 to 6 carbon atoms, and
R is normal alkyl having 1 to 6 carbon atoms.
2. The chemical compound of claim 1, wherein J is methyl, and R is ethyl.
* * * * *